United States Patent [19]

Marlett

[11] Patent Number: 4,748,260
[45] Date of Patent: May 31, 1988

[54] PREPARATION OF AMINE ALANES

[75] Inventor: Everett M. Marlett, Baton Rouge, La.

[73] Assignee: Ethyl Corporation, Richmond, Va.

[21] Appl. No.: 945,286

[22] Filed: Dec. 22, 1986

[51] Int. Cl.$^4$ ............................................. C08F 5/06
[52] U.S. Cl. ................................... 556/176; 556/170; 556/171
[58] Field of Search .................. 556/176, 170, 171

[56] References Cited

U.S. PATENT DOCUMENTS

| | | | |
|---|---|---|---|
| 2,680,059 | 6/1954 | Bragdon | 23/14 |
| 2,955,126 | 10/1960 | Rosco et al. | 556/176 |
| 3,159,626 | 12/1964 | Ashby | 260/242 |
| 3,326,955 | 6/1967 | Brendel et al. | 556/176 |
| 3,479,382 | 11/1969 | Brendel | 556/176 |
| 3,535,107 | 10/1970 | Nelson et al. | 556/176 X |
| 3,541,125 | 11/1970 | Sims | 556/176 |
| 3,642,853 | 2/1972 | Murib et al. | 556/176 |
| 3,646,086 | 2/1972 | Sims | 556/176 |
| 3,764,666 | 10/1973 | Murib | 556/170 X |
| 3,891,686 | 6/1975 | Ehrlick et al. | 556/176 |
| 3,926,833 | 12/1975 | Hoffman et al. | 252/188 |
| 4,006,095 | 2/1977 | Hoffman et al. | 252/188 |
| 4,064,153 | 12/1977 | Cucinella et al. | 556/176 X |
| 4,474,743 | 10/1984 | Martett | 423/347 |
| 4,665,207 | 5/1987 | Martett | 556/176 |

OTHER PUBLICATIONS

Brown et al, J.A.C.S., 88, 1464–1472 (1966).
Ruff et al, JACS, 82, 2141 (1960).
Ashby, Adv. Inorg. Chem. Radiochem 8, pp. 295 & 310 (1966).

Primary Examiner—Paul F. Shaver
Attorney, Agent, or Firm—John F. Sieberth; Robert A. Linn

[57] ABSTRACT

Process for the preparation of silane and a tertiary amine alane, said process comprising reacting about equimolar amounts of:
 (a) an alkali metal aluminum tetrahydride having the formula $MAlH_4$, wherein M is an alkali metal selected from the class consisting of lithium, sodium and potassium,
 (b) a hydrogen halide, and
 (c) a complexing tertiary amine.

In this process, $NaAlH_4$, HCl, and $(C_2H_5)_3N$ are preferred reactants. The amine alane product can be reacted with a silicon halide to prepare silane.

10 Claims, No Drawings

PREPARATION OF AMINE ALANES

BACKGROUND OF THE INVENTION (1) Field of the Invention

The invention pertains to the formation of amine alanes, $AlH_3.NR_3$. These materials are useful as chemical intermediates. For example, they can be reacted with a silicon halide such as $SiCl_4$ or $SiF_4$ to produce silane.

(2) Related Art

Reference is made to U.S. Pat. No. 4,474,743. It pertains to production of silane and aluminum fluoride from silicon tetrafluoride and amine alanes. Reference is also made to U.S. Pat. No. 4,006,095. It teaches, inter alia, that $SiCl_4$ reacts with a toluene solution of $AlH_3$ containing dimethyl ether or a stabilizing amine.

U.S. Pat. No. 4,474,743, cited above, contains a citation to U.S. Pat. No. 4,006,095. It also sets forth other prior art relating to amine alane production. For example, it sets forth the following general methods for preparing amine alanes:

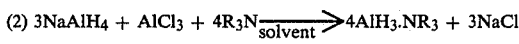

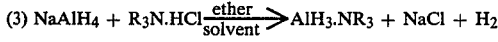

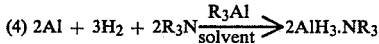

U.S. Pat. No. 4,474,743 also states that:

"Alane, that is aluminum trihydride or $AlH_3$, has in the past been produced from the reaction of $LiAlH_4$ and $AlCl_3$ in ethers. Also known is the production of an alane dimethyl ether solution from the reaction of LiH and $AlCl_3$ in dimethyl ether, catalyzed by $NaAlH_4$.

Amines are used to produce amine alanes for subsequent syntheses. For example, $LiAlH_4$ can be reacted with a trialkyl amine.HCl complex to precipitate LiCl and form $AlH_3.NR_3$ where R is alkyl."

Of particular interest is the reaction given by Equation (3). As illustrated by the equation, it is known that amine hydrochlorides can react with sodium aluminum hydride to prepare amine alanes, sodium chloride, and hydrogen. This reaction is similar to that using $LiAlH_4$ reported in the paper by Ruff et al, *J. Am. Chem. Soc.* 82 pp 2141-2144 (1960).

The process of the instant invention is distinct from the process of Equation (3) since the instant process does not use pre-formed amine hydrochlorides. In other words, the process of this invention comprises bringing together in uncombined form, an amine and a hydrogen halide (such as HCl) for reaction with a complex metal aluminum hydride. Thus for example, the process of this invention can be conducted by forming a mixture of alkali metal aluminum hydride and tertiary amine, and then adding the hydrogen halide to the aforesaid mixture. Alternatively, the process of this invention can be conducted by adding an alkali metal aluminum hydride such as $NaAlH_4$ to a reaction zone, and then simultaneously (or substantially simultaneously) adding the amine and hydrogen halide of choice to the complex metal hydride, thereby causing the added starting materials to react and form the products of this invention.

The process of this invention is not obvious from the prior art. In fact, it is contrary to what the art suggests. Thus, Ruff et al, loc cit suggests to a skilled practitioner that it is necessary to use a pre-formed amine hydrochloride. Ashby *"The Chemistry of Complex Aluminohydrides": Adv. Inorg. Chem. Radiochem.* 8 (1966) pp. 295 and 310, teaches that protic and halogen acids would react violently with $LiAlH_4$ to liberate hydrogen. On the other hand, Brown, et al *J. Am. Chem. Soc.* 88 1464-72 (1966) reports that 100% sulfuric acid can be added to a THF solution of $LiAlH_4$ to evolve hydrogen and produce a solution of aluminum hydride. However, in neither case was any evidence presented as to what would occur when the acid is added to a suspension of the complex aluminum hydride in an inert solvent such as toluene. From a combination of the Ruff et al, and Ashby references, a skilled practitioner might conclude that the process of this invention would not work, since the complex metal hydride and the hydrogen halide could interact in a deleterious way, making them both unavailable for reacting according to the process of this invention.

The process of this invention is conducted by contacting the reactants under reaction conditions. Furthermore, as indicated above, it does not require pre-formed amine hydrochlorides used in the art. Thus, in one aspect, the invention comprises a process for reacting a complex metal hydride, an amine, and a hydrogen halide; said process being conducted in the substantial absence of added pre-formed amine hydrohalide.

The process of this invention does not require an ether reaction medium utilized by Ruff et al. Although, the process of this invention can be conducted in the presence of an ether, it is preferred that it be conducted in the substantial absence of ethers.

CROSS REFERENCE TO RELATED APPLICATION

Application Ser. No. 782,972, filed Oct. 2, 1985, teaches formation of amine alane complexes by reacting: (a) an alkali metal aluminum hydride with (b) an alkali metal tetrachloride or tetrabromide, and (c) a complexing tertiary amine.

SUMMARY OF THE INVENTION

This invention comprises a process in which an amine alane is formed by reacting: (i) HCl, or HBr, or similar substance, (ii) a complexing tertiary amine, and (iii) an alkali metal aluminum hydride, $MAlH_4$, wherein M is Li, Na or K. The amine alanes produced by this invention can be reacted to form silane, for example by using the method of U.S. Pat. No. 4,474,743, cited above. Silane is an important article of commerce. It is used in the production of semiconductor devices. It is also used as an intermediate for the formation of polysilicon; that substance is also employed in the production of semiconductors.

DESCRIPTION OF PREFERRED EMBODIMENTS

This invention pertains to the preparation of a tertiary amine complex of aluminum trihydride. Stated another way, this invention comprises a process for the preparation of a tertiary amine alane. The process of this invention comprises reacting substantially equimolar amounts of:

(a) an alkali metal aluminum tetrahydride having the formula MAlH$_4$, wherein M is an alkali metal selected from the class consisting of lithium, sodium and potassium,
(b) a hydrogen halide, and
(c) a complexing tertiary amine.

Without being bound by any theory, it is believed this process can be illustrated by the following equation, in which sodium aluminum tetrahydride and triethylamine are reacted with HCl.

(5)
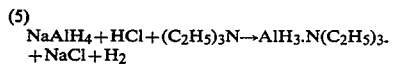
NaAlH$_4$+HCl+(C$_2$H$_5$)$_3$N→AlH$_3$.N(C$_2$H$_5$)$_3$.+NaCl+H$_2$ This process is preferably conducted in the presence of a liquid reaction medium. Excess tertiary amine and hydrocarbons are examples of suitable liquid media. Toluene is a preferred hydrocarbon reaction medium.

As taught above, this invention comprises reacting a complex metal aluminum hydride. As indicated above, the preferred complexes have the formula MAlH$_4$, wherein M is an alkali metal. All three alkali metal compounds, LiAlH$_4$, NaAlH$_4$ and KAlH$_4$ can be used. In commerce, KAlH$_4$ is not readily available at this time; hence LiAlH$_4$ and NaAlH$_4$ are preferred. The sodium compound is much cheaper than the lithium analog, LiAlH$_4$, hence use of NaAlH$_4$ is more preferred. The sodium compound can be used admixed with a hydrocarbon. Furthermore, the compound Na$_3$AlH$_6$ can be used in this invention in a manner analogous to NaAlH$_4$. Thus, its reaction with a hydrogen halide such as HCl, and a tertiary amine such as triethylamine (to produce hydrogen, sodium chloride and an amine alane) is considered an embodiment of this invention.

In the process of this invention illustrated by Equation (5), HCl is used. Other materials can also be used in this process; e.g. HF, HBr, and HI, and the like.

This invention is conducted using a tertiary amine that forms an amine alane by complexing with aluminum hydride, AlH$_3$. For purposes of describing this invention, the amines that are so employed are referred to herein as "complexing tertiary amines". Suitable complexing tertiary amines which may be utilized in the invention are liquids or low melting solids and include tertiary aryl, cyclic, alkyl, alkenyl and aralkyl amines, including monoamines, diamines, triamines, etc. Typically, the amines of the present invention may be tetramethylethylenediamine, diphenylmethylamine, triethylenediamine, phenylmethylethylamine, tricyclohexylamine, or mixtures thereof, and other similar compounds. A more preferred class of amines for use in the invention are aliphatic tertiary amines, which include trialkylamine and trialkenylamine. Further, these amines may generally contain up to about 30 carbon atoms each, and preferably contain alkyl and alkenyl groups each having from 1 to about 10 carbon atoms. Thus, useful amines of this class are tri-n-butylamine; tri-sec-butylamine; dibutylpentylamine; n-butyl-octyl-secbutylamine; tripentylamine; trihexylamine; trihexenylamine; trioctadecylamine; didecenylpentylamine; and the like, as well as mixtures thereof. Some unsaturation in the alkenyl amines may be reduced by the hydrogen produced in the process. A most preferred class of amines for use in the invention are those in the lower alkyl amines such as trimethylamine, triisopropylamine, and particularly, triethylamine. By the term "lower" is meant that the alkyl groups each contain 6 carbon atoms or less. The above compounds may be readily prepared by procedures well known to those skilled in the art. Products of the present invention are these amines complexed with aluminum hydride.

Also usable complexing amines are the tertiary polyamines such as N,N,N',N'-tetramethylethylenediamine and 1,4-diazabicylco[2.2.2]octane. Other tertiary mono- and polyamines are suitable, such as tri-n-propylamine, triisopropylamine, ethyldimethylamine, diethylmethylamine, tributylamine, dimethylpropylamine, N,N,N,',N'-tetramethyldiaminomethane, quinuclidine, methyl-1,4-diazabicyclo[2.2.2]octane, etc.

As indicated above the complexing amines usable with the invention include the trialkylamines especially tri-loweralkylamines such as trimethylamine and triethylamine. Trimethylamine is a gas at room temperature and is therefore more difficult to use in some of the preparations of amine alane. Triethylamine is the most preferred complexing tertiary amine of the invention. It forms a weak complex with the AlF$_3$ co-product produced upon reacting the amine alane product of this invention with SiF$_4$ according to the method of U.S. Pat. No. 4,474,743, such that less amine is complexed therewith and moderate heating affords vaporization of the amine.

The starting materials that react in the process of this invention combine in equimolar quantities, as given in equation (5) above. A skilled practitioner will readily appreciate that it is not necessary to conduct the process of this invention using exactly equimolar amounts. For example, the process can be conducted while approximating these quantities. Alternatively, one may use an appreciable excess of one or more reactants. For example, an excess of the amine—if the amine is a liquid—can be used as a reaction medium.

In light of the above, a skilled practitioner will appreciate that the molar ratio employed is an important, but not a critical feature of this invention. In general, it is usually desirable to carry out the invention in an economical manner. Therefore, it will usually be desirable to use the reactants in a manner such that they are not wasted. Furthermore, in most instances they should be used in amounts that do not unduly encumber product recovery and separation. Excessive quantities of starting materials can waste them, and might make product recovery unduly complicated. Therefore, in many instances equimolar amounts, or close approximations thereof will be used. The process is preferably conducted using the starting material MAlH$_4$ as the limiting reactant.

In this invention, use of a liquid reaction medium is normally preferred. Liquid media facilitate contacting the reactants. Also, a liquid aids the mixing and contacting of reactants even when the reactants are not appreciably soluble in the liquid medium. Hydrocarbons and amines illustrate the types of materials that can be used as liquid reaction media in this invention. Suitable amines are exemplified by those mentioned above.

A wide variety of liquid hydrocarbons can be used as reaction media in this invention. Aromatic hydrocarbons are a preferred class of liquid reaction media and toluene is highly preferred.

Other useful aromatic hydrocarbons are benzene, ethylbenzene, propylbenzene, butylbenzene, meta-xylene, para-xylene, ortho-xylene, 1,2-diethylbenzene, 1,3-diethylbenzene, 1,4-diethylbenzene, 1,3-dipropylbenzene, 3-propyltoluene, 4-ethyltoluene, 4-propyltoluene, 4-butyltoluene, the trimethylbenzenes, and trialkylbenzenes generally. Also suitable are liquid polycyclic aromatic hydrocarbons such as 1-methylnaphthalene, tetrahydronaphthalene, and the like.

Another class of hydrocarbon reaction medium usable with the invention includes the alkanes such as pentane, hexane, heptane, octane, nonane, decane, undecane, dodecane, and the like.

It will also be understood by a skilled practitioner that the use of a liquid reaction medium is a preferred, but not a critical feature of this invention. Thus as taught or inferred above, the use of a reaction liquid facilitates contacting the reactants, as well as facilitating the operations of transferring the reaction mass, and separation of products therefrom. For these purposes, inert liquid reaction media that are relatively inexpensive are preferred. Other factors in choice of the liquid include solubility of the reactants, boiling point, level of toxicity, etc.

When $NaAlH_4$ is used to prepare the amine alane, a relatively pure source is desirable, especially where trace metals are present. Thus for example, the $NaAlH_4$ is preferably recrystallized if the $NaAlH_4$ is prepared from aluminum containing titanium; e.g., 1900 ppm titanium. Otherwise, a catalyzed autodecomposition of the alane may occur if the crude mixture is heated or allowed to stand for long periods. Crude $NaAlH_4$ can be used successfully if the product solution of $AlH_3.NR_3$ is filtered from the by-product salts and other impurities.

The reaction conditions, temperature, pressure, and reaction time are important, but not critical aspects of this invention. In general, a skilled practitioner will select a set of reaction conditions which affords an acceptable product yield in a reasonable reaction time, without an untoward amount of undesired side reactions. The process conditions selected will in some way or ways reflect the ingredients employed. For example, if trimethylamine is used as a reactant, the reaction can be conducted at somewhat elevated pressure to facilitate contacting this amine with the other materials in the reaction mixture. If a starting material is somewhat temperature sensitive, a low to mild temperature can help diminish decomposition of the sensitive substance. If the reaction kinetics are slow, a longer reaction time can be used to increase reaction yields.

The set of reaction parameters employed can be selected by a skilled prac:titioner without an undue amount of experimentation using the skill of the art and the teachings within this specification.

The process of this invention can be conducted over a wide range of temperatures. A suitable temperature range is about 5° C. to about 50° C. and a preferred range is about 10° to about 35° C. The process can be conducted at atmospheric, sub-atmospheric or superatmospheric pressures. In general, atmospheric pressure is suitable when using reactants that are solids or liquids at reaction temperatures. A preferred pressure range is 1 to 100 atmospheres, more preferably 1 to 20 atmospheres. The reaction time is not a truly independent variable but is dependent at least to some extent on the other reaction conditions employed. Generally, the process is conducted using a reaction time of from 0.25 to 24 hours, preferably from about 1 to about 8 hours.

The following examples illustrate the process but do not limit it.

EXAMPLE I

To a 100 mL, 3-neck, round bottom flask was charged:
 7.2 g $NaAlH_4$ slurry, in toluene, (74.4% solids, ~85%, ~0.084 mole)
 37.7 g toluene
 8.18 g triethylamine ($Et_3N$) (99%, 0.080 mole)

A HCl gas generator was devised using a 100-mL, 3-neck, round bottom flask equipped with a magnetic stirrer, dry ice condenser to trap water formed, and a dispensing funnel swept with a nitrogen purge. To the 100-mL flask was charged 4.68 g NaCl (0.080 mole), and to the funnel was charged 40.0 g of conc. $H_2SO_4$.

The flask with the $NaAlH_4$ was cooled in an ice bath and the $H_2SO_4$ was dripped into the NaCl. The HCl produced, and a $N_2$ sweep, was conducted via a short length of Tygon tubing to a feed line with entry below the $NaAlH_4$/toluene/amine level.

The HCl gas was introduced over a period of about 5 minutes while maintaining the reaction temperature at 1°-6° C. Formation of a fluffy material was initially noted at about 20 minutes. After about 55 minutes into the run, the temperature of the reactor was allowed to slowly increase. Over a period of 95 minutes, the temperature increased to 21° C. and the reaction was stopped. During the course of the reaction period, additional fluffy material was noted.

The reaction mixture was filtered leaving a filter cake approximately 1.0 cm×3.0 cm. By analysis, the fluff was shown to be triethylamine hydrochloride. Analysis of the filtrate (39.1 g)—by determination of the hydrogen produced via acidic hydrolysis—indicated that the yield of triethylamine alane ($Et_3N.AlH_3$) was 71%. The filtrate contained 3.26% Al, and this indicated the yield of amine alane product was 71.7%.

The procedure of this example can be repeated using a reaction temperature of about 5° C. to about 50° C. and using $LiAlH_4$ or $KAlH_4$ in place of the $NaAlH_4$ employed. Similar results are obtained.

The procedure of the above example can also be repeated using, in place of triethylamine, trimethylamine, tri-n-propylamine, tri-n-butylamine, N,N,N',N'-tetramethylethylenediamine.

Other amines that can be made to react according to the process of the previous example are:
 triethylenediamine (Dabco),
 N,N,N',N'-tetramethyldiaminomethane,
 N-methylpyrrolidine,
 2-methyltriethylenediamine, and
 quinuclidine.

EXAMPLE II

The procedure of this example was similar to the procedure of the previous example. This time, a small $H_2SO_4$ scrubber was placed between the HCl generator and the $NaAlH_4$ flask, in order to trap $H_2O$ produced in the HCl generation procedure. Also, an adaptor was fitted to the $NaAlH_4$ flask, in order to trap any triethylamine hydrochloride formed, in the vapor space, so that it could be washed back into the reaction mixture.

The reaction flask was charged with:
 5.00 g $NaAlH_4$ (90.4%, dry, 0.0837 mole or ~5% excess)
 40.0 g toluene
 8.60 g triethylamine ($Et_3N$) (99%, 0.084 mole, 5% excess)

The HCl generator was charged with 4.68 g of NaCl and the funnel with 40.0 g conc. $H_2SO_4$ (22 mL). Reaction was initiated by starting $H_2SO_4$ addition and sweeping the HCl produced into the $NaAlH_4$ flask, which was initially at a temperature of 10° C. C. The temperature slowly increased during the HCl addition to 15° C. The $H_2SO_4$ addition time was about 58 minutes. At about 23 minutes into the run, gel formation in the $NaAlH_4$ flask was noted.

After the 58-minute period noted above, the cold water bath was removed from around the $NaAlH_4$ flask, and the temperature rose to 21° C. after 35 additional minutes. At that time, the gel broke, and the trapped triethylamine hydrochloride was washed down into the reaction mixture. The reaction mixture was maintained at 21°–23° C. for 2 hours and 15 minutes after the amine hydrochloride was washed back into the flask. Then, the reaction mixture was removed to the dry box and filtered.

The filtrate weighed 45.84 g. The yield of triethylamine alane product, by gas evolution analysis, was 87.2%, and by aluminum analysis, was 88.1%.

EXAMPLE III

The procedure of this example was similar to the procedures in the previous examples. This time, a dry ice trap followed the $H_2SO_4$ scrubber to stop any $H_2SO_4$ aerosol or moisture from entering the hydride reactor.

The 100-mL, 3-neck, round bottom flask was charged with:
- 7.11 g $NaAlH_4$ slurry in toluene, (~75% solids, ~85% pure, ~0.084 mole)
- 33.7 g toluene
- 10.12 g triethylamine ($Et_3N$) (0.100 mole; 25% excess)

The HCl generator was charged with 4.68 g of NaCl, and the funnel with 40.0 g conc. $H_2SO_4$.

The $H_2SO_4$ addition to the NaCl was complete in an hour. The HCl produced was swept into the reaction flask with $N_2$ while maintaining the temperature of the reaction mixture at 15°–18° C. The reaction temperature was allowed to rise to 25° C. over a 2-hour period after the $H_2SO_4$ addition was complete.

After filtration, 42.88 g of filtrate was recovered. Analysis indicated the yield of triethylamine alane was:
- 90.8% (gas evolution analysis)
- 93.6% (Al analysis)

Apparently, the excess amine increased the reaction yield by compensation of volatilization losses or some other mechanism.

EXAMPLE IV

In the procedure of this example, trimethylamine was used as the complexing amine. It was added to the hydride reaction flask underneath the surface of the $NaAlH_4$/toluene mixture, at a site inside the flask opposite the site where HCl was introduced. A dry ice, cold finger condenser was fitted to the reaction flask to condense any trimethylamine ($Me_3N$) that volatilized, and to prevent $Me_3N.HCl$ from escaping. There was used:
- 7.11 g $NaAlH_4$ slurry in toluene (~75% solids, ~85% pure, ~0.084 mole)
- 37.9 g toluene
- 5.6 g trimethylamine ($Me_3N$) (0.095 mole)

The HCl generator was charged with the same charge of NaCl and $H_2SO_4$ as in the previous example. During the course of reactant addition, the temperature of the reactor mass was maintained at 15°–17° C. The trimethylamine was added over a period of 32 minutes and the $H_2SO_4$ over a period of 45 minutes. (The addition of both reactants was started at the same time.) The $H_2$ sweep was maintained after all $H_2SO_4$ had been added, and at roughly one hour after $H_2SO_4$ addition was complete, some trimethylamine hydrochloride that had formed above the liquid level was knocked back into the reaction flask. Also, after a total elapsed time of one hour (after reaction initiation), the temperature was allowed to increase slowly. At the end of a total time of two hours, the reaction was stopped.

The filtrate weighed 42.62 g. Analysis indicated the yield of trimethylamine alane was:
- 77.2% per gas evolution analysis
- 74.3% per aluminum analysis The procedure of this example can be repeated using a reaction temperature of about 0° C. to about 50° C. and using $LiAlH_4$ or $KAlH_4$ in place of the $NaAlH_4$ employed. Similar results are obtained.

EXAMPLE V

In this example, the trimethylamine was added to the sodium aluminum hydride and toluene. After the amine was charged, HCl addition was initiated. The HCl was generated as before from NaCl and $H_2SO_4$. There was used:
- 7.11 g $NaAlH_4$ slurry in toluene (~75% solids, ~85% pure, ~0.084 mole)
- 37.9 g toluene
- 5.9 g trimethylamine (0.100 mole)
- 4.68 g NaCl (0.080 mole)
- 40.0 g conc. $H_2SO_4$ The amine was added over a period of 16 minutes and then the $H_2SO_4$ addition initiated, and maintained for 45 minutes. The ice bath was removed after a total elapsed time of two hours and one hour later the reaction was stopped.

The reaction mixture was filtered; and the filtrate found to weigh 41.73 g. Aluminum analysis indicated the yield of trimethylamine alane was 59.4%.

While preferred embodiments have been described above, various aspects of the invention may be altered without departing from the scope or spirit of the invention as defined by the appended claims.

We claim:

1. Process for the preparation of a tertiary amine alane, said process comprising reacting about equimolar amounts of:
   (a) an alkali metal aluminum tetrahydride having the formula $MAlH_4$, wherein M is an alkali metal selected from the class consisting of lithium, sodium and potassium,
   (b) a hydrogen halide, and
   (c) a complexing tertiary amine.

2. The process of claim 1 being conducted in the presence of a hydrocarbon reaction medium.

3. The process of claim 2 wherein said hydrocarbon reaction medium is toluene.

4. The process of claim 1 wherein said tetrahydride is sodium aluminum tetrahydride, $NaAlH_4$.

5. Process for the preparation of triethylamine alane, said process comprising reacting $NaAlH_4$, HCl and $(C_2H_5)_3N$.

6. The process of claim 5 being conducted in the presence of toluene as a liquid reaction medium, and at a temperature of from about 5° C. to about 50° C.

7. Process for the preparation of trimethylamine alane, said process comprising reacting NaAlH₄, HCl and (CH₃)₃N.

8. Process of claim 7 being conducted in the presence of toluene as a liquid reaction medium and at a temperature of about 0° C. to about 50° C.

9. The process of claim 1 being conducted in the substantial absence of an ether.

10. The process of claim 1 being conducted in the substantial absence of preformed amine hydrohalide.

* * * * *